US005342752A

United States Patent [19]
Platz et al.

[11] Patent Number: 5,342,752
[45] Date of Patent: Aug. 30, 1994

[54] METHOD OF INACTIVATION OF VIRAL BLOOD CONTAMINANTS USING ACRIDINE DERIATIVES

[75] Inventors: Matthew S. Platz, Columbus, Ohio; Raymond P. Goodrich, Jr., Pasadena, Calif.; Victoria A. Wong, Cary, N.C.

[73] Assignee: Cryopharm Corporation, Pasadena, Calif.

[21] Appl. No.: 686,334

[22] Filed: Apr. 16, 1991

Related U.S. Application Data

[63] Continuation-in-part of Ser. No. 510,234, Apr. 16, 1990.

[51] Int. Cl.$^5$ .............................................. A01N 1/02
[52] U.S. Cl. .......................................... 435/2; 514/297
[58] Field of Search ............................ 435/2; 514/297

[56] References Cited

U.S. PATENT DOCUMENTS

| | | | |
|---|---|---|---|
| 3,333,583 | 8/1967 | Bodell | 128/142 |
| 4,071,412 | 1/1978 | Eisenberg | 195/102 |
| 4,268,279 | 5/1981 | Shindo | 55/16 |
| 4,325,715 | 4/1982 | Bowman | 55/158 |
| 4,409,105 | 10/1983 | Hayashi | 210/678 |
| 4,684,521 | 8/1987 | Edelson | 424/101 |
| 4,748,120 | 5/1988 | Wiesehahn | 435/173 |
| 4,870,018 | 9/1989 | Lehmann | 435/240.1 |
| 4,874,690 | 10/1989 | Goodrich | 435/2 |
| 4,878,891 | 11/1989 | Judy | 604/5 |
| 4,950,665 | 8/1990 | Floyd | 514/222.8 |
| 4,973,327 | 11/1990 | Goodrich | 604/408 |

OTHER PUBLICATIONS

Lin, L. et al, Blood, 74:517–525 (1989).
Sun, I. et al, J Clin Microbiology 8:604–611 (1978).
Cryobiology, vol. 10, issued 1973, D. Pribor, "Studies with Dextran 40 in cryopreservation of blood", pp. 93–103, see entire article.
Acta Vet Scand, vol. 20, issued 1979, V. Myhrvoid, "Cryopreservation of sheep red blood cells", pp. 531–536, see entire article.
R. Acheson et al., "Acridines" published 1956 by Interscience Publishers, Inc. (N.Y.), pp. 339–361, see pp. 352–355.
Mutation Research, vol. 81, issued 1981, W. Firth et al., "Azido Analogs of Acridine: Photoaffinity Probes for Frameshift Mutagenesis in *Salmonella typhimurium*", pp. 295–309, see p. 299.
Vox Sang, vol. 26, issued 1974, K. Ganshirt et al., "A Five-bag system for washing fresh erythrocytes and their preservation", see p. 66.
Vox Sang, vol. 55, issued 1988, G. Espersen et al., "Irradiated Blood Platelet Concentrates Stored for Five Days—Evaluation by in vitro Tests", pp. 218–221, see abstract.
Pharm. Delt. Epistom. Eksosis, vol. 1, No. 2, issued 1971, J. Polak et al., "The Bactericidal and Fungicidal Activity of Some Quinolinium Compounds", pp. 27–33. See entire article.
Exp. Parasitol., vol. 31 issued 1972, C. Lantz et al., "*Plasmodium berghei:* Inhibited Incorporation of AMP-8-$^3$H into Nucleic Acids of Erthrocyte-Free Malarial Parasites by Acridines, Phenanthridines, and 8-Aminoquinolines", pp. 255–261, see p. 258.

*Primary Examiner*—Douglas W. Robinson
*Assistant Examiner*—S. Saucier
*Attorney, Agent, or Firm*—Heller, Ehrman, White & McAuliffe

[57] ABSTRACT

A method is provided for inactivating viral and/or bacterial and/or parasitic contamination in cellular blood matter or blood plasma protein fractions, using radiation sensitizing chemical compounds and irradiation with, for example, UV radiation.

7 Claims, No Drawings

METHOD OF INACTIVATION OF VIRAL BLOOD CONTAMINANTS USING ACRIDINE DERIATIVES

This is a continuation-in-part of Ser. No. 07/510,234 filed Apr. 16, 1990, the disclosure of which is incorporated by reference herein in its entirety.

FIELD OF THE INVENTION

This invention relates to the general field of biochemistry and medical sciences, and specifically to inactivation of viral contamination of blood cell compositions comprising peripheral blood cells (red blood cells, platelets, etc.), and plasma protein fractions (albumin, clotting factors, etc.) purified from collected whole blood.

BACKGROUND OF THE INVENTION

A major concern in the transfusion of donated, stored whole human blood or the various blood cells or protein fractions isolated from whole blood is the possibility of viral contamination. Of particular concern are the blood-borne viruses that cause hepatitis and acquired immune deficiency syndrome (AIDS). While any number of cell washing protocols may reduce the viral contamination load for samples of blood cells, by physical elution of the much smaller virus particles, such washing alone is insufficient to reduce viral contamination to safe levels. In fact, some viruses are believed to be cell-associated, and unlikely to be removed by extensive washing and centrifugal pelleting of the cells. Current theory suggests that safe levels will ultimately require at least a 6 log (6 orders of magnitude) demonstrated reduction in infectious viral titer for cellular blood components. This 6 log threshold may be greater for plasma protein components, especially the clotting factors (Factor VIII, Factor IX) that are administered throughout the life of some hemophilia patients.

Viral inactivation by stringent steam sterilization is not acceptable since this also destroys the functional components of the blood, particularly the blood cells and plasma proteins. Dry heat sterilization, like wet steam, is harmful to blood cells and blood proteins at the levels needed to reduce viral infectivity. Use of stabilizing agents such as carbohydrates does not provide sufficient protection to the delicate blood cells and proteins from the general effects of exposure to high temperature and pressure.

Methods that are currently employed with purified plasma protein fractions, often followed by lyophilization of the protein preparation, include treatment with organic solvents and heat or extraction with detergents to disrupt the lipid coat of membrane enveloped viruses. Lyophilization (freeze-drying) alone has not proven sufficient to inactivate viruses, or to render blood proteins sufficiently stable to the effects of heat sterilization. The organic solvent or detergent methods employed with purified blood proteins cannot be used with blood cells as these chemicals destroy the lipid membrane that surrounds the cells. In addition, the safety of existing commercial preparations of such treated plasma protein components may be in question, since many hemophilia patients who routinely receive injections of clotting protein fractions subsequently develop hepatitis.

Another viral inactivation approach first demonstrated in 1958 has involved the use of a chemical compound, beta-propiolactone, with ultraviolet (U.V.) irradiation. This method has not found acceptance in the United States due to concern over the toxicity of beta-propiolactone in the amounts used to achieve some demonstrable viral inactivation.

It is therefore a desideratum to devise an effective viral inactivation treatment for human blood components, which will not damage the valuable blood cells or proteins. The treatment must be selective for viruses, while allowing the intermingled blood cells or proteins to survive unharmed. The treatment must also be non-toxic (i.e., any added chemicals must be used in amounts that will not cause toxicity upon subsequent injection).

While the present invention is concerned with viral inactivation, it is understood that the same concepts and uses disclosed herein can also apply to inactivation of blood-borne bacterial contaminants, or to blood-borne parasitic contaminants. All such infectious organisms rely on nucleic acids for their growth and propagation. Since purified blood plasma protein fractions are substantially free of human nucleic acids, and mature human peripheral blood cells, particularly red blood cells and platelets lack their own DNA, the use of nucleic acid-binding sensitizers is especially useful for the problem of treating blood contaminants.

SUMMARY OF THE INVENTION

The present invention provides a method for the selective viral inactivation of human blood compositions, as opposed to the less selective methods of heat, organic solvents, or detergents that are harmful to cells and proteins. The present invention utilizes a class of compounds based on acridine dyes, which comprise a relatively low toxicity class of compounds, and which can selectively bind to the nucleic acid (single-stranded DNA, double-stranded DNA, or RNA) that comprises the genetic material of viruses. The bound compound can be activated by brief exposure to radiation, such as ultraviolet radiation (U.V. light of a defined wavelength), after which the activated compound attacks and damages the bound viral nucleic acid, rendering the virus sterile and non-infectious. Activation of the selectively bound chemical compound (which serves as a radiation sensitizer) focuses the reaction chemistry to the viral nucleic acid, and limits exposure to nearby cellular components or plasma proteins.

According to the present invention, a radiation sensitizing chemical compound is added to a liquid suspension of infectious viruses, and the mixture is exposed to U.V. light. Assays of viral infectivity demonstrate the effectiveness of the compounds in inactivating the viruses, compared to radiation treatment alone. The treatments disclosed utilize liquid suspensions of model viruses (bacteriophages that normally infect bacteria), but the concepts and utility of the present invention can also be applied to human viruses, including viruses found in human blood or blood components. The concepts and utility of the present invention can also be applied to lyophilized or lyophilized and rehydrated blood components, in particular red blood cells, platelets, and plasma protein fractions.

Depending upon the nature of the presumed radiolytic mechanism of the sensitizer reaction with the virus, other types of radiation may be used, particularly penetrating or ionizing radiation, such as, gamma-radiation, X-ray radiation, etc., provided the energy, wavelength, and frequency are tuned to the particular radiation-absorbing sensitizing compound to achieve efficient activation of the compound.

Activation is thought to involve the generation of chemical free radicals via the interaction of the sensitizer with the radiation energy, and it is the chemical radicals that then react with nearby molecules, in particular bound nucleic acids. The selective binding of the sensitizing compound to nucleic acid acts to bring into close physical proximity the relevant chemical reactants: the viral nucleic acid and the chemical radicals generated by radiation-induced activation. This mechanism provides the selective basis for the present invention, which is an improvement over use of radiation alone, which, like heat treatments or solvent-detergent treatments, causes widespread damage to many biological molecules (including lipids, proteins, and carbohydrates).

The chemical sensitizers utilized in accordance with the present invention include those of the formula:

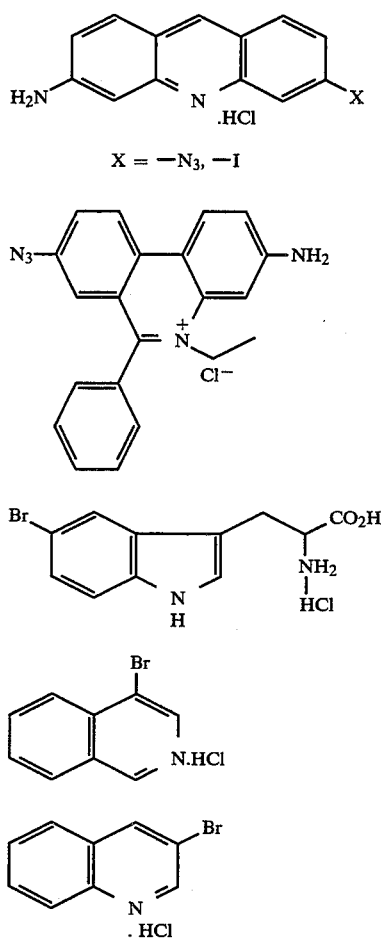

The preparations of these compounds (I–VI) are known. See Martin, R. F. and Kelly, D. P. *Aust. J. Chem.*, 32,2637–46(1979); Firth, W. and Yielding, L. W. *J. Org. Chem.*, 47,3002(1982).

Without being bound by theory, the specific compounds listed above represent a general class of chemical compounds that may find application as radiation sensitizers for viral inactivation, particularly inactivation of viruses found in infected human whole blood or cellular or protein components derived from human blood. This broad class of chemical compounds shares the properties of selective binding to nucleic acids, and is capable of reacting with impinging radiation energy while in the bound state to yield activated states that can chemically react with bound nucleic acid, thereby damaging the nucleic acid and rendering the entire virus particle sterile, inactive, and non-infectious.

DESCRIPTION OF THE PREFERRED EMBODIMENTS

The method of the invention is applicable to erythrocytes (RBC's) platelets, hemosomes or other blood or blood-like cells. The erythrocytes, platelets or other cellular matter may be obtained from commercial sources or may be prepared by known methods from whole blood by centrifugation, removal of the plasma supernatant and resuspending the pellets in PBS.

Alternatively, commercially available packed blood cells may be used, which typically are prepared in CPDA (commercial solution containing citrate, phosphate, dextrose and adenine).

Typically, the cells will be mixed with a sufficient amount (based on total dry weight of cells) of the chemical sensitizer. Preferably, in a composition of packed red blood cells about 0.001 to 1 mg of the chemical sensitizer will be used per ml. of packed cells. Preferably, the mixture will be irradiated with UV radiation at the preferred wavelength of 320 nm. Preferred exposure is from 1–10 minutes, preferably about 3 minutes.

To show useful application against viruses, the following preferred working example is provided.

Compounds I–III, synthesized according to published methods, are finally suspended in a solution of dextrose-saline containing 5 mM dextrose and 0.9% wt/vol NaCl, a preferred diluent for human red blood cells for transfusion. Each compound is suspended at a concentration of 1 mg/ml. Aliquots of each compound in dextrose saline are then mixed with a suspension of active bacteriophage, either bacteriophage lambda or bacteriophage phi-X 174.

Bacteriophage lambda is representative of a general class of protein-coated, double-stranded DNA virus. Bacteriophage phi-X174 is representative of a general class of protein-coated, single-stranded DNA virus.

The mixture of live bacteriophage, at a starting infectious titer of at least 10E7 plaque-forming units (PFU)/ml, and sensitizing compound in dextrose-saline, is then exposed to ultraviolet radiation, preferably having a wavelength of 320 nanometers (nm), for a period of time, preferably 3 minutes, in a quartz chamber that is transparent to U.V. light. The irradiated mixture is then added to a suspension of live host bacteria, and the entire mixture (or ten-fold serial dilutions of the mixture) are then spread onto petri dishes containing bacterial growth agar.

Live infectious bacteriophage lambda or phi-X174 cause infected host cells to lyse, leaving a clear spot or "plaque" on the opaque lawn of confluent cell growth. This plaque assay allows a sensitive and simple measure of the number of infectious viruses present in the original mixture.

Having described the preferred embodiments of the present invention, the following examples are provided by way of illustration but are not intended to limit the invention in any way.

EXAMPLE 1

Packed human red blood cells purified from donated whole blood are washed free of the anticoagulant storage solution (commercially available CPDA, containing citrate/phosphate/dextrose/adenine), and suspended in dextrose-saline at a 10% hematocrit. Approximately 10 ml of washed packed red cells is placed in a quartz chamber and exposed to U.V. light, preferably at 320 nm, for 2 minute time intervals, up to a 10 minute total exposure. At each 2 minute interval the suspension is mixed and a small sample of red cells (10 microliters) is removed and diluted into 2 ml of water for spectrophotometric assay of hemoglobin. At each step the temperature of the irradiated red cell suspension is measured, to ensure that the suspension did not overheat. At no point did the suspension exceed 26 degrees C. (normal body temperature is 37 degrees C.). Untreated red cells contain a high proportion of functional oxyhemoglobin (oxyHb), usually in the range of 96% or higher. Oxidation damage can form a semi-stable methemoglobin species (metHb), which can normally be reduced back to oxyhemoglobin by a cellular repair enzyme. Hemichrome represents a more severely damaged form, and can be irreversible. Normal red cells can tolerate a moderate level of methemoglobin. Hemichrome degradation can produce free heme, the iron-porphyrin component of native hemoglobin, which is damaging to cell membranes. Thus it is desirable to minimize hemichrome levels. Each hemoglobin species can be detected at a specific wavelength, using a standard spectrophotometer.

The following data show the sensitivity of the hemoglobin to damage by the increased U.V. exposure. An exposure of 3 minutes was judged to be usable for viral inactivation using a radiation sensitizer, without inflicting excessive damage to red blood cells.

| EXPOSURE (Minutes) | % OXYHB | % METHB | % HEMI |
| --- | --- | --- | --- |
| 0 | 96.6 | 3.4 | 0 |
| 2 | 90.2 | 7.5 | 2.3 |
| 4 | 84.5 | 13.4 | 2.1 |
| 6 | 76.7 | 22.5 | 0.9 |
| 8 | 72.6 | 27.4 | 0 |
| 10 | 66.4 | 33.6 | 0 |

EXAMPLE 2

An aqueous suspension of live bacteriophage lambda and live bacteriophage phi-X174, each having a starting infectious titer known to be at least 10E7 PFU/ml, is exposed to incident radiation ranging in wavelength from 190 nm to 450 nm. At each incident radiation wavelength, absorbance by the bacteriophage suspension is monitored. No appreciable absorption occurs by the suspension of each virus alone at 320 nm, the preferred wavelength for use with the sensitizing compounds. Therefore, the viruses and their predominant molecular components (viral coat proteins and nucleic acid) do not absorb well in the desired wavelength. Use of a sensitizer is needed to increase the absorbance by the virus in the desired wavelength.

EXAMPLE 3

A preparation of 0.1 ml of a suspension of bacteriophage lambda or bacteriophage phi-X174, of at least 10E7 PFU/ml, is separately added to 4 ml of dextrose-saline containing 1 m−ml of compounds I or II or Ill. Each suspension of bacteriophage with a radiation sensitizing compound is then exposed to U.V. radiation of the preferred wavelength (320 nm) in a quartz chamber for the preferred time (3 minutes). A control sample of each bacteriophage suspension, containing a sensitizer, is not exposed to U.V. light. Serial dilutions are performed to quantitate the level of infectious titer, and aliquots of the various bacteriophage samples are then mixed with host bacteria and spread on nutrient agar. Following a normal growth period, the plates are assayed for plaques. Other bacteriophage suspensions are separately irradiated as above, but without added sensitizer, to demonstrate the effect of this dose of U.V. alone.

| COMPOUND | Log10 Reduction of Virus Titer | |
| --- | --- | --- |
|  | phi-X174 | Lambda |
| I (X = N3) | >6.0 | >6.0 |
| I (X = I) | 4.0 | >6.0 |
| II | 1.7 | >6.0 |
| No compound | 2-3 | 2-3 |

From these data it can be seen that all three tested compounds significantly increase the sensitivity of double-stranded DNA virus (lambda) to U.V. of the preferred exposure. Compound II is also effective against a single-stranded DNA virus, phi-X174. Compound I is most preferred, showing a high (at least 6 log reduction) inactivation efficacy against both single-strand and double-strand DNA viruses.

What is claimed is:

1. A method of reducing parasitic contamination in blood matter comprising red blood cells, platelets, blood plasma protein fractions or mixtures thereof comprising the steps of:

(a) contacting said blood matter in vitro with a chemical sensitizer of the formulas:

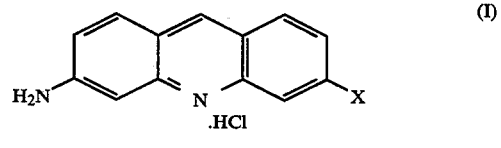

$$X = -N_3, -I$$

(b) exposing said blood matter and chemical sensitizer to radiation of sufficient energy and wavelength for a period of time sufficient to cause said sensitizer to substantially inactivate the parasitic contamination in said blood matter.

2. A method according to claim 1 wherein said blood matter comprises red blood cells.

3. A method according to claim 1 wherein said blood matter comprises platelets.

4. A method according to claim 1 wherein said radiation comprises ultraviolet radiation.

5. A method according to claim 1 wherein said parasitic contamination comprises single- and/or double-stranded type viruses.

6. A method according to claim 1 wherein said blood matter comprises blood plasma proteins.

7. A method according to claim 1 wherein said parasitic contamination comprises bacterial contamination.

* * * * *

UNITED STATES PATENT AND TRADEMARK OFFICE
CERTIFICATE OF CORRECTION

PATENT NO: 5,342,752
DATED: August 30, 1994
INVENTORS: Matthew S. Platz, Raymond P. Goodrich and Victoria A. Wong It is certified that an error appears in the above-identified patent and that said Letters Patent is hereby correct as shown below:

On the title page, item [54], please replace "DERIATIVES" with --DERIVATIVES--.

On the title page, item [56], after the last U.S. patent document, please insert --
FOREIGN PATENT DOCUMENTS
--JP 61-275228  12/86   Japan--".

In column 1, line 4, replace "DERIATIVES" with --DERIVATIVES--.

In column 1, after line 4, please insert --This work was partially supported by the United States Government through the National Institute of Health under Grant No. GM 3482308. The United States Government may have certain rights in this invention.

RELATED APPLICATIONS--.

Column 5, line 46, please delete "10E7" and insert --$10^7$--.

Column 5, line 62, please delete "10E7" and insert --$10^7$--.

Signed and Sealed this

Sixteenth Day of December, 1997

*Attest:*

BRUCE LEHMAN

*Attesting Officer*    *Commissioner of Patents and Trademarks*